United States Patent [19]

Mardi et al.

[11] Patent Number: 4,595,591
[45] Date of Patent: Jun. 17, 1986

[54] USE OF DILUTE NITRIC ACID SOLUTIONS FOR TREATING CERTAIN SKIN LESIONS

[75] Inventors: Shalva Mardi, Binningen; Heinz F. Lichti, Riehen; Guido Baumgartner, Bettingen, all of Switzerland; Daniel Garteiz, Cincinnati, Ohio; Claude I. Judd, Loveland, Ohio; Murray Weiner, Cincinnati, Ohio

[73] Assignee: Solco Basel AG, Basel, Switzerland

[21] Appl. No.: 464,371

[22] Filed: Feb. 7, 1983

Related U.S. Application Data

[63] Continuation-in-part of Ser. No. 362,794, Mar. 29, 1982, abandoned, which is a continuation of Ser. No. 191,465, Sep. 26, 1980, abandoned.

[30] Foreign Application Priority Data

Sep. 27, 1979 [CH] Switzerland ............... 8713/79

[51] Int. Cl.$^4$ .................................................. A61K 7/48
[52] U.S. Cl. ........................................ 424/127; 424/132; 424/140; 424/145; 252/DIG. 5
[58] Field of Search ................. 252/DIG. 5; 424/127

[56] References Cited

PUBLICATIONS

Kirk–Othmer, Encyclopedia of Chemical Technology, Second Edition, Wiley Pub., vol. 13, pp. 810–813, (1967).
Ryabov et al., Chemical Abstracts, vol. 87, No. 5, abst. No. 34,084s, Aug. 1, 1977.
Stedman's Medical Dictionary, Twenty Third Edition, Williams and Wilkins Co., Pub. pp. 346 and 861, (1976).
Remington's Pharmaceutical Sciences, p. 1379, Fourteenth Edition Mack Publishing Co. 1970.
Chemical Abstracts, vol. 16, (1), p. 538, Jan. 10, 1922.

Primary Examiner—Alan L. Rotman
Attorney, Agent, or Firm—Ladas & Parry

[57] ABSTRACT

The composition consists of an aqueous solution of nitric acid and nitrous acid with a pH below 1 and an acid equivalent of from 6 to 10 mmole/ml; the amount of nitrous acid corresponds to 0.01 to 5 mg of nitrite ($NO_2^-$) per ml. Additionally, the solution preferably contains acetic acid, oxalic acid and lactic acid as well as copper and cadmium ions. For the preferred composition, the preparation takes place by mixing the components and letting them react to the end or by an oxidative method, in the course of which nitrous acid is formed. The composition is suitable for the local treatment of superficial lesions of the skin and mucous membranes in the fields of cosmetics and medicine, particularly for certain malignant tumors. Experimentally, the effectiveness can be checked by two biological tests developed for this purpose.

1 Claim, No Drawings

USE OF DILUTE NITRIC ACID SOLUTIONS FOR TREATING CERTAIN SKIN LESIONS

CROSS-REFERENCE TO RELATED APPLICATIONS

This application is a continuation-in-part of Ser. No. 06/362,794 filed Mar. 29, 1982 (abandoned), which in turn is a continuation of Ser. No. 06/191,465 filed Sept. 26, 1980 (abandoned).

For centuries, caustic agents, in particular strong acids, have been used to "burn out" cutaneous lesions, warts and the like. However, not all strong acids are equally popular—presumably because of the quite varying nature of their effects on integumental proteins.

Thus, particularly, concentrated solutions of nitric acid, furthermore salicylic acid and some halogenated acetic acids [H. W. Felter, The Eclectic Materia Medica Pharmacology and Therapeutics, John K. Scudder Publisher, Cincinnati (OH, USA), 1922, page 133; A. L. Welsh, The Dermatologist's Handbook, C. C. Thomas Publisher, Springfield (USA) 1957, page 111; C. J. Lunsford et al, Arch. Dermat. and Syph. 68 (1953), 148] have gained more or less specific niches in the armamentarium of dermatologists, while hydrochloric acid, for example, is rarely used.

Still with the purpose of burning out warts, lactic acid and oxalic acid have been proposed too (H. W. Felter, loc. cit.) as well as acetic acid (F. P. Foster, Practical Therapeutics, D. Appleton and Co., 1897, page 226). The keratolytic effect of these acids, however, is small and they are therefore almost always used in combination with salicylic acid (German Publ. Patent Appln No. 1,266,448). For example, a composition is being sold in the USA under the name of Compound W Wart Remover, which contains acetic acid and salicylic acid (Handbook of Nonprescription Drugs, 5th edition, American Pharmaceutical Association 1977, pages 364 and 368). More recently, U.S. Pat. Nos. 3,920,835 and 3,988,470 disclosed a composition comprising glycolic acid, citric acid, malic acid, tartronic acid, tartric acid, glucuronic acid, pyruvic acid, methyl pyruvate, ethyl pyruvate, 2-hydroxiisobutyric acid or 3-hydroxybutyric acid, which alleviates the symptoms of hyperkeratinization conditions, e.g. acne and palmar or plantar hyperkeratosis.

As is well known, however, the treatments with caustic agents often leave more or less ugly scars (R. Volk and F. Winter, Lexikon der kosmetischen Praxis, Julius Springer Editor, Vienna 1936, page 677; K. O. Möller, Pharmakologie, 2nd German edition, Benno Schwabe & Co., Basle 1953, pages 167 and 584).

The therapeutical use of caustic agents for treating skin cancer is expressly declined (R. Volk and F. Winter, loc. cit., page 308), because of too great a risk of not completely removing the carcinoma; afterwards, it is often noticed that an insufficiently treated carcinoma suddenly begins to again proliferate rapidly.

On the other hand, in the 19th century, various metallic salts have been proposed for removing warts and other skin defects, among others copper salts like the acetate and the sulfate, lead salts in combination with zinc sulfate, copper sulfate and white vinegar, furthermore antimony, arsenic, chromium, mercury and silver salts (C. J. Lunsford, loc. cit.) as well as cadmium salts [S. O. L. Potter, Therapeutic Materia Medica and Pharmacy, P. Blakiston's Son and Co., Philadelphia (PA, USA) 1909 page 185]. Among all these salts, only zinc chloride when used together with trichloroacetic acid—Mohs' method—has reached some short-lived importance for treating skin cancer.

At last, in USSR Inventorship Certificate 229,744 (granted in 1969; A. Z. Karchauli), an agent for treating benign tumors and precancerous diseases of the skin is disclosed, which consists of a mixture of copper nitrate and lactic acid. The preparation is carried out by mixing copper nitrate containing nitric acid and lactic acid in the proportions 1:2 and 3:1. However, experimental followup work with this agent has evidenced an instability which can be such as to cause bursting of the bottle.

A new composition has now been found, with which superficial lesions of the skin and of the mucous membranes of benign, premalignant and malignant type can be successfully treated; the composition display its effect upon topical application.

Among the above-mentioned lesions are first of all lesions and tumors of the skin and of the mucous membranes which are detrimental to the bodily beauty, but which in the vernacular do not constitute illnesses, e.g. warts, birth-marks, naevus, haemangioma and callus' due to age, but also benign skin diseases and finally precanerous conditions and malignant tumors.

The composition according to the invention consists of an aqueous solution which comprises (1) nitric acid in a concentration and amount which gives the solution a pH value of below about 1 and an acid equivalent of from about 6 to 10 millimole/ml, and (2) a metal nitrite which is soluble in aqueous nitric acid, or nitrous acid, in an amount equivalent to about 0.01 to 5 mg of nitrite ($NO_2^-$) per ml, and which, when stored at room or lower than room temperature, proves stable as regards the respective range of concentration of components 1 and 2.

Since the new composition is a strongly acidic one, comparisons with other acids or strongly acidic preparations were appropriate in order to better understand the role of each of its main features and the reasons for its excellent effect. For this purpose, two specific biological tests were expressly developed. As shown in detail in the following, the cosmetic and therapeutic effectiveness actually runs parallel with positive results in the tests.

I. In vitro test

If white hair, human or animal, e.g. rat hair, is dipped into the composition, it quickly turns bright yellow, while the solution itself remains colorless; the hair retains its structural integrity. This "fixing" of the hair with simultaneous color-change apparently reflects a chemical reaction, as a consequence of which the tissue viability is lost, but its anatomical structure is largely retained; the tissue is "mummified".

Contrary thereto, hydrochloric acid in a concentration of 20 to 35% (weight/weight) does not "yellow" but dissolves the hair in a few hours (depending on the concentration used). 10% acetic acid—a recognized topical treatment for warts—does not "yellow" the hair.

II. In vivo test

As any chemist knows from experience, brief application to the skin of concentrated nitric acid produces a yellow-brown coloration which does not disappear for a week or more. If less strong (33.4%) nitric acid is applied to the skin for less than 1 minute, it produces no or a hardly visible reaction. If such acid is left to act for 2 minutes, a stinging sensation is felt for some minutes, but there is no other immediate reaction; several minutes later there is an erythematous reaction which becomes maximal in about 15 to 45 minutes and then disappears without trace after one to two hours.

In contrast, if the composition of this invention, which is of similar acid strength, is similarly applied to normal human skin, a characteristic tan discoloration appears which persists for days. Sometimes, a small neighboring area of skin develops a slight transient erythema. To test for this effect, 10 $\mu$l (0.01 ml) of solution is applied to the inside of the forearm and wiped away after two minutes.

If one compares in these two tests the composition and nitric acid solutions of the same and other concentrations, the following is shown:

TABLE 1

| (Rat hair) | |
| --- | --- |
| Nitric acid 33.4%* (6.2 normal), alone | Yellowing after at least 30 minutes |
| idem, +3 mg/ml NaNO$_2$ [acc. to the invention] | Yellowing in 1 to 2 minutes |
| idem, +8.9 mg/ml Cd(NO$_2$)$_2$ [acc. to the invention] | Yellowing, 1-2 minutes** |
| idem, +0.6 mg/ml NaNO$_2$ [acc. to the invention] | Yellowing, 2-3 minutes |
| Nitric acid 17.8% (3.1 normal), alone | No discoloration in 48 hours |
| idem, +3 mg/ml NaNO$_2$ [acc. to the invention] | Yellowing, 10-13 minutes |
| Nitric acid, 6.1% (1.0 normal), alone | No discoloration in 48 hours |
| idem, +3 mg/ml NaNO$_2$ [acc. to the invention] | Very slight yellowing, 116-134 minutes no increase in color intensity in 48 hours |
| conc. HNO$_3$ (65%; 14.3 normal), alone | Yellowing in 1 to 2 minutes fast dissolution of hair, forming a yellow solution |
| NaNO$_2$, 10 mg/ml, alone | No discoloration in 48 hours |

*All percentages are in weight/weight
**The "times" in minutes mean the time of the last negative observation-time of the first positive observation

TABLE 2

| (Human skin, inside of forearm) | | | |
| --- | --- | --- | --- |
| A. 3 minutes reaction time | | | |
| | After minutes: | After days: | |
| Nitric acid 33.4% | pink coloring (erythema) | no further traces | |
| idem + 3 mg/ml NaNO$_2$ [acc. to the invention] | brown coloring | light brown coloring | |
| B. 2 minutes reaction time | | | |
| | Immediately after: | After 1 hour: | After 2 hours: | After 7 hours: |
| Nitric acid 33.4% | no reaction | clear pink spot (erythema) | pink spot, just visible | no further traces |
| idem + 8.9 mg/ml Cd(NO$_2$)$_2$ [acc. to the invention] | brown spot | the brown spot remains* | | |

*practically unchanged even after 48 hours

The peculiar, until now quite unknown biological effect of the composition according to the invention and the remarkable role the nitrous acid plays are clearly seen from the tables. As compared to a comparable solution of nitric acid, the tests show a significant difference which is reflected exactly in the results of the clinical trials.

On the whole, the composition produces—measured on the discoloration of the hair and skin—a chemical reaction as fast as that of concentrated nitric acid, but without the strong caustic effect of this and other acids which dissolve all tissues indiscriminately. During the reaction of the composition, the integumental proteins are immediately denatured in situ and the anatomical structure is fixed intravitally (mummified), without being altered or injured.

The remarkable function of the metal nitrite or the nitrous acid in the composition can also be impressively substantiated by adding urea to the composition; urea is known to decompose the nitrous acid. If a sufficient amount of urea is added, the positive reaction in the in vitro test is fully suppressed.

TABLE 3

| (Rat hair) | |
| --- | --- |
| Nitric acid 33.4% + 3 mg/ml NaNO$_2$ [acc. to the invention] | yellow discoloration in 1 to 2 minutes |
| idem + 2 mg/ml urea | yellow discoloration, 4-5 minutes |
| idem | yellow discoloration, |
| + 10 mg/ml urea | 234-264 minutes |

The negative influence of the urea can also be seen in the in vivo test. If urea is added at a ratio of 10 mg per ml to the composition according to the invention mentioned in Table 3, before application to the human skin, no color reaction occurs.

According to an advantageous embodiment of the invention, the aqueous solution has an acid equivalent of from about 8.0 to about 9.5 millimol/ml; besides this, its pH-value preferably is below about 0. The composition generally contains about 300 to about 600 mg of pure nitric acid per ml.

Suitable as metal nitrite are, among others, sodium and potassium nitrite due to their being readily available and proportionable. While the lower limit of component (2), calculated as nitrite (NO$_2^-$), lies at about 0.01 mg/ml, an upper limit cannot be unambiguously determined. As Table 4 shows, an increase of the nitrite content beyond 3 mg/ml does not appear worthwhile as no faster discoloration of the rat hair is achieved thereby. Preferably, a maximum amount of about 5 mg/ml should not be exceeded.

TABLE 4

| (Rat hair) Addition of sodium nitrite to nitric acid 33.4% | | | | | | |
| --- | --- | --- | --- | --- | --- | --- |
| NaNO$_2$ in mg/ml | 0 | 0.08 | 0.5 | 1.5 | 3.0 | 4.0 | 5.0 |
| Yellow coloring (in minutes) | 207-242 | 146-206 | 15-22 | 2-3 | 1-2 | 1-2 | 1-2 |

From the table, the minimal effectiveness of the composition is at a nitrite contents in the range of from 0.1 to 0.5 mg/ml, when evaluated from the reaction of a healthy, strong tissue (rat hair). As will be shown later, the reaction of a cutaneous lesion or pathologically altered tissue takes place more quickly and strongly than that of a normal integument. For this reason, the minimal effectiveness in the in vitro test should correspond to optimal effectiveness in clinical and cosmetic application. A composition with a nitrate content of from about 0.1 to 0.5 mg/ml is therefore preferred.

Surprisingly, it has proved particularly advantageous, in view of the contents and therefor also of the effect of the composition if it also contains an organic carboxylic acid which can be oxidized by nitric acid. Particularly suitable therefor are aliphatic hydroxy acids, ketonic acids and unsaturated acids such as lactic acid, oxalic acid, glycolic acid, glyoxylic acid, malic acid, tartaric acid, dimethylmaleic acid, 2-hydroxy butyric acid, tartronic acid, mesoxalic acid, citric acid, citraconic acid and glucuronic acid.

With the nitric acid, such organic acids form reduction products, such as nitrous gases and nitrous acid, in amounts sufficient to ensure the necessary minimal concentration of nitrite in the composition and thus to retain thereby the chemical composition according to the invention at all events. It is known that the speed of oxidation of oxidizable organic acids is different, depending on their chemical structure; for instance pyruvic acid is quickly oxidized by nitric acid, but oxalic acid slowly, while lactic acid takes up the middle position in this respect. It is therefore advantageous to add to the composition a mixture of organic acids which are oxidizable at varying speeds, appropriately pyruvic acid, lactic acid and oxalic acid; this will then guarantee the desired nitrite content for a longer period of time.

The peculiar role of the oxidizable carboxylic acids for the maintenance of the composition within the given limit values, however, is not exhausted with the new formation of nitrous acid by the mentioned oxidation/reduction reaction. From these acids and the nitric and nitrous acid, particularly during the oxidative method of preparation described below, are formed certain condensation products, such as esters and anhydrides, e.g. O-nitryl- and O-nitrosyl derivatives of lactic acid and O-lactyl lactic acid. These compounds prove to be relatively unstable, i.e. they tend to slowly decompose, regenerating the nitrous acid, according to the level of equilibrium in the solution and have thereby a stabilizing effect.

Anyway, the aqueous solution can contain, besides the oxidizable carboxylic acids, further organic acids which exhibit a keratolytic effect. Suitable herefor are among others, acetic acid, halogenated acetic acid, salicylic acid etc. The composition, however, often already has its own keratolytic effect because certain oxidizable carboxylic acids, e.g. pyruvic acid and lactic acid, have this effect per se.

The composition therefore preferably contains lactic acid—e.g. in an amount of about 4 to 40 mg/ml, oxalic acid—e.g. in an amount of about 20 to 60 mg/ml, and acetic acid—e.g. in an amount of about 10 to 50 mg/ml, optionally also pyruvic acid—e.g. in an amount of about 1 mg/ml.

As another facultative component, the aqueous solution can advantageously contain a metal salt which, when applied topically, is not toxic and which is soluble in nitric acid solution at a pH below about 1. Such metal salts which can particularly be considered are those of copper, silver, cadmium, zinc, aluminium, calcium, strontium, magnesium, iron—preferably iron(III), antimony, bismuth, selenium, manganese, zirconium, cobalt, gold, titanium and tin. The corresponding nitrates are preferred.

Of the said metal ions, copper, silver, cadmium and zinc ions have proved particularly suitable; with copper ions, $Cu^{++}$ is preferred for practical reasons. The aqueous solution can then contain up to about 0.1 mg copper ions per ml, or up to about 6 mg of silver ions per ml, or up to about 3.5 mg of cadmium ions per ml, or up to about 6 mg of zinc ions per ml. More than one of these metal ions can also be present simultaneously, e.g. copper and cadmium ions, silver and zinc ions, copper and silver ions or copper, cadmium and zinc ions.

Especially preferred is the embodiment of the composition, in which the aqueous solution contains—besides the nitric acid and the nitrous acid—acetic acid, oxalic acid, lactic acid as well as cadmium ions and copper ions, these components preferably being present in the aforementioned concentrations and the solution having the aforementioned pH-value and the given acid equivalent. Such a composition is described in more detail in Examples 2 and 7 to 10.

The preparation of the composition can simply take place by the mixing process, i.e. by merely mixing the components together. With the above-mentioned, preferred composition, the dissolution can take longer due to the differing solubilities of the starting products; to accelerate the procedure it is therefore advantageous to stir continuously while adding the components. Appropriately, the organic acids and the inorganic salts, preferably nitrates, are first dissolved in water and 65% nitric acid (specific weight about 1.41) is then slowly added to the aqueous solution; the solution is then brought to the desired concentration with water and optionally sodium nitrite is added. If, after a few days, crystals have separated from the solution, they are removed by filtration.

However, the preparation by an oxidative process is preferred, in which the nitrite is not added but is formed in sufficient amounts in the solution by oxidation of the organic carboxylic acids. In addition to nitrous gases resp. nitrous acid, condensation products are formed from the organic carboxylic acid in amounts sufficient to provide the stabilizing or self-regenerating effect. Two compositions of comparable composition were produced by the mixing resp. oxidative processes and were tested regularly for a period of 11 to 113 days (at room temperature) with the biological in vitro test (rat hair); the speed of the yellow coloration was seen to hardly decrease with the "oxidative" product, whereas the product of the mixing process showed a distinctly larger loss of activity.

The self-regeneration, in particular of the composition produced by oxidation, can easily be followed with the in vitro test, as will be shown in the following table on the composition of Example 7.

TABLE 5

| Storage conditions | (Rat hair) Time of test | Yellow coloration of the rat hair, in minutes |
|---|---|---|
| sealed container* | at the beginning | <1 |
|  | after 13 days | <1 |
|  | after 18 days | <1 |
| seal removed | at the beginning | <1 |
|  | after 23 minutes | 1-2 |
|  | after 2 hours | 12-18 |

TABLE 5-continued

(Rat hair)

| Storage conditions | Time of test | Yellow coloration of the rat hair, in minutes |
|---|---|---|
|  | after 5½ hours | 77-104 |
| container sealed again | after 25 hours | 26-30 |

*only opened to quickly take sample

Furthermore, it was also found that the composition of the solutions, namely in respect of the nitrite and oxalate content, tended in time towards similar or comparable values, whether the composition was prepared by mixing with the addition of a nitrite or by the oxidative process. It is important thereto that the containers are not sealed hermetically during storage but have a loose seal. This slow convergence of the composition of preparations resulting from different production processes is illustrated in detail in Example 11; it gives the composition according to the invention a substantial unity within the given limit values.

Still further starting products, such as metals, simple esters of the said carboxylic acids, and glucose, which can be converted into the required end products by oxidation, can be used in the preparation by the oxidative method. If the preferred composition is produced according to this method, one can generally proceed as follows.

A mixture of nitric acid, copper nitrate and cadmium nitrate, acetic acid, lactic acid and oxalic acid is prepared. Copper nitrate or cadmium nitrate can be produced in situ by dissolving metallic copper or cadmium in nitric acid or in a mixture containing nitric acid. Acetic acid, lactic acid and oxalic acid can also be added in the form of their lower alkyl esters, e.g. as ethyl esters. In addition, the ethyl esters of acetic acid, lactic acid or oxalic acid can, at least in a small proportion, be produced in situ by adding ethanol to the mixture of the free acids.

Generally, the oxidative method is carried out in that lactic acid or ethyl lactate, oxalic acid or diethyl oxalate, acetic acid or ethyl acetate and optionally ethanol are added in any optional order to a solution containing copper ions and cadmium ions in concentrated nitric acid and is allowed to react at a slightly to moderately increased temperature.

A preferred embodiment of this method consists of dissolving concentrated nitric acid, a water-soluble copper(II)-salt, preferably copper(II)-nitrate, or metallic copper and a water-soluble cadmium salt, preferably cadmium nitrate, or metallic cadmium together or allowing them to react, adding lactic acid or ethyl lactate and optionally aqueous ethanol to the solution obtained and letting it react, adding oxalic acid or ethyl oxalate and then acetic acid or ethyl acetate to the solution obtained and letting the solution react to completion. During the whole period of preparation, the temperature is kept at room temperature to slightly increased temperature, preferably 20° to 40° C., by respective cooling or heating.

A further embodiment consists of preparing a mixture from lactic acid or ethyl lactate, oxalic acid or ethyl oxalate, acetic acid or ethyl acetate, ethanol, a water-soluble cadmium salt, preferably cadmium nitrate and a water-soluble copper(II)-salt, preferably copper(II)-nitrate; after substantial dissolution, as appropriate by heating to a moderate temperature, nitric acid is added at room temperature and the mixture is left to react to completion at a moderate temperature.

A still further embodiment consists of preparing a mixture of lactic acid or ethyl lactate and anhydrous ethanol and adding consecutively concentrated nitric acid, oxalic acid or diethyl oxalate, acetic acid or ethyl acetate, a water-soluble cadmium salt, preferably cadmium nitrate, a water-soluble copper(II)-salt, preferably copper(II)-nitrate, and water; in the solution obtained, the reaction is started and left to react to completion by alternate heating to moderate temperature and leaving to stand at room temperature for a longer period.

When following these embodiments, the heat supply and the duration of the reaction can be chosen or increased in such a way that the final concentration of lactic acid is considerably reduced and the maintenance of the concentrations within the mentioned ranges at room temperature is increased. If desired, uniformity of the final composition, resp. its conformity with the requirements according to the invention can be achieved by further adding some other components, such as e.g. oxalic acid and a nitrite.

In any case, the reaction is left to react until the liquid has become clear and colorless and has a pH-value below about 1 and hardly any more bubbles form, which generally requires 2 to 3 months; the supernatant liquid is then separated from the solid phase which is discarded.

For example, 20 ml of glacial acetic acid, 1 g of oxalic acid dihydrate, 205 g of 90% lactic acid, 20 to 25 ml of anhydrous ethanol, 1 g of maleic acid and 15 ml of pyruvic acid can be taken with 900 to 1000 ml of 65% nitric acid.

The quantitative analysis of the examples produced by the oxidative method and a series of further examples according to the mentioned embodiments gave the following range for the respective values and contents; the following nominal ranges for the composition and characteristics of the final solution can be derived therefrom:

TABLE 6

|  | Range found experimentally | Nominal Range |
|---|---|---|
| Specific weight | 1219-1312 | 1200-1320 mg/ml |
| Acid equivalent | 7.38-10.3 | 6.0-10.0 mmol/ml |
| Dry weight* | 632-931 | 600-950 mg/ml |
| Content of $Cd^{2+}$ | 1.34-2.15 | 1.3-2.3 mg/ml |
| Content of $Cu^{2+}$ | 0.007-0.055 | 0.006-0.060 mg/ml |
| Oxalate content | 28-45 | 25-60 mg/ml |
| Lactate content | 0-45 | 0-50 mg/ml |
| Nitrate content | 349-519 | 300-600 mg/ml |
| Nitrate content | 0.0001-25.93 | 0.01-5 mg/ml |
| Acetic acid content | 21-47 | 20-50 mg/ml |
| Ethanol | 0 | 0 or trace |

*after neutralization and lyophilisation

The preferred composition then consists of an aqueous solution, the components of which correspond to the above nominal range; this composition has proved excellent in cosmetical and clinical trials.

Such a composition was also tested in the in vitro and in vivo test, as will be shown in the following tables. In the in vitro test, the significant role of the nitrous acid was confirmed, both in comparison to a corresponding solution of pure nitric acid and by adding urea. Equally striking is the similar comparison in the in vivo test, by applying 0.01 ml of the solutions of human skin.

TABLE 7

(Rat hair)

| | |
|---|---|
| Composition of Example 7 [acc. to the invention, oxidative method] | yellow coloration in 1 to 2 minutes |
| idem, + 10 mg/ml urea | yellow coloration 186–206 minutes |
| Nitric acid 33,4% | yellow coloration, 210–230 minutes |
| Nitric acid 33.4% + 3 mg/ml NaNO₂* [acc. to the invention, mixing method] | yellow coloration in 1 to 2 minutes |

*for comparison; already listed in Table 2A.

TABLE 8

(Human skin, inside of forearm)

2 minutes reaction time

| | immediately after | after 1 hour | after 2¾ hours | after 7 hours |
|---|---|---|---|---|
| Composition of Example 7 [acc. to the invention, oxidative method] | brown spot | the brown spot remains* | | |
| idem + 10 mg/ml urea | no reaction | distinct pink spot (erythema) | distinctly pink but lighter | no further traces |
| Nitric acid 33.4% | no reaction | definite clear pink spot | pink spot hardly visible | no further traces |
| Nitric acid 33.4% + 8.9 mg/ml Cd (NO₂)₂⁺ [acc. to the invention, mixing method] | brown spot | the brown spot remains* | | |

*Practically unchanged even after 48 hours
⁺for comparison; already listed in Table 2B The composition according to the invention constitutes a clear, colorless liquid. If it is stored in an open container at room temperature, the biological tests turn negative in less than 2 weeks, apparently due to the decomposition of the nitrous acid. A practically unlimited stability can be achieved by storage between 0° and 10° C., e.g. in the refrigerator, preferably at about 4° C. and in a loosely closed container.

The mentioned stability does not mean a numerical constancy of the nitric acid and nitrate contents and even less a numerical constancy of the contents of other components: it is primarily the range of concentration provided by the invention with respect to nitric acid and the nitrite ($NO_2^-$) which is decisive for the beneficial effects proved in the field of cosmetics and in the clinics. As far as these components are present in the mentioned range of concentration and which ever may be the changes occuring within said range in course of time, the action of the composition is assured.

It is also possible without difficulty to offer the composition in the form of two vials, the first containing a sodium nitrite solution, the second a solution of the other components or the first the nitric acid, the second the lactic acid, ethanol and the other components and to mix the contents of the two vials together before use.

The new composition has been tested in animal experiments (rabbits) for its local tolerance. It proved not to result in significant reaction beyond the site of application; on the (previously shaved) areas of treated skin, the hair grows again as it does on the untreated control animals. In addition thereto, no systemic effects at all could be found.

The composition should be applied on the one hand in the field of cosmetics, on the other hand in medicine. The cosmetic range of indications extends to all non-malignant skin defects which are cosmetically detrimental and as long as these are superficial and do not exceed a certain size. In the cosmetic field, the composition should only be used by specialists who have first been introduced to its method of application and mode of action in a special course.

The main fields of use in medicine are suitable indications in dermatology, oncology, urology, ophthalmology and gynaecology. The composition should only be applied superficially, by the doctor or on his instructions and under his control by experienced medical staff, but on no account by the patients themselves.

The composition must be applied strictly locally, by topical or other forms of local treatment onto resp. into the pathologically altered part of the tissue which one wishes to remove. Beginning in the middle of the lesion and extending outwards to the periphery, one or more droplets of the composition are distributed and worked into the lesion by light pricking. This special type of local application plays a considerable part in the success of the treatment and forms an integral part of the invention.

Pointed wooden sticks, e.g. tooth picks, and thin porous plastic sticks or felt-pen tips, among others of polyethylene or polypropylene, have proved especially suitable as applicators. As already mentioned, the composition can be in the form of two vials of differing contents; the applicators mentioned now make a second, equally simple embodiment of this principle possible. The porous sticks can be dipped into a nitrite solution and then carefully dried; shortly before use, the stick impregnated with the nitrite is dipped into the solution of the other components.

In this way, tooth picks of wood or pointed plastic sticks, e.g. of polypropylene, singly or in bundles are dipped into a 13% (weight/weight) cadmium nitrite solution and dried. A 33.4% (weight/weight; 6.2 normal) nitric acid solution is stirred with the impregnated sticks and then subjected to the in vitro test with rat hair. The hair turns yellow in less than 1 to 2 minutes, thus showing the nitric acid solution to contain enough nitrite for complying with the required composition. The same sticks can then be dipped into the nitrite-containing solution and be used as applicators, to apply this freshly prepared solution to the lesion.

This embodiment can be carried out advantageously as follows. A solution of a metal nitrite which is soluble in aqueous nitric acid, for instance an aqueous 10% sodium nitrite solution, is put into a vessel, e.g. a Petri dish, in which the desired depth of exposure can be controlled. The applicator sticks are placed vertically into this solution, for example 1 cm deep for 15 minutes, and then lifted out and allowed to dry in vertical position.

Using the speed of yellow coloration of white rat hair as an index, it was demonstrated that thus impregnated applicator sticks—whether they are made of wood, or a hard, in the normal use of language non-porous, plastic, or a very porous plastic—fulfill the purpose: if they are dipped into 0.3 ml of a 6.2 normal nitric acid solution for 15 seconds, four days after impregnation, this solution then shows a nitrite contents according to the invention (Table 9).

TABLE 9

(Rat hair)

| Applicator material | Time to yellow (minutes)* |
|---|---|
| Untreated wood | 207–297 |
| NaNO$_3$ treated wood (control) | 119–204 |
| NaNO$_2$ treated wood | 4–6 |
| Untreated non-porous plastic | 293–383 |
| NaNO$_3$ treated non-porous plastic (control) | 95–170 |
| NaNO$_2$ treated non-porous plastic | 4–5 |
| Untreated porous plastic | 180–270 |
| NaNO$_2$ treated porous plastic | 1–3 |

*Time of the last negative observation - time of the first positive observation

For the dosage and duration of application of the composition, the place, size and thickness of the cutaneous lesion and the degree of its callosity must be taken into consideration. Usually, 0.05 to 0.1 ml of the solution are needed for the treatment. Skin lesions of more than 10 mm diameter should only be treated after it has been ensured that only superficial skin sections are concerned. The number of lesions treated simultaneously and their total area should not exceed 4 to 5 and 5 cm$^2$, respectively. More than 0.25 ml should not be used during one sitting. If the mummificiation is unsatisfactory, a second treatment can take place 3 to 4 days later. If a larger number of cutaneous lesions are involved, the treatment is to be carried out in several sittings at 4-week intervals.

It is recommendable to treat only for a few minutes at first, to wait a short time for the reaction and then to proceed with treatment depending on the intensity of the reaction until the local discoloration is completely developed and the lesion begins to shrink slightly.

The methods common at this time for the treatment of various skin tumors, namely electrocauterization, cryo-surgery as well as radiotherapy and chemotherapy or plastic surgery are not always fully satisfactory. Malignant tumors or those suspected of being malignant are excised deeply out of the healthy tissue, mostly after sample excision. Such a procedure and sometimes necessary plastic surgical measures are particularly difficult near the eyes or in the nose region or not possible at all in the case of multiple lesions and recurrences, e.g. in an area previously treated by radiotherapy. The method of Mohs which after prior treatment with trichloroacetic acid and zinc chloride allows the successive removal of the pathological tissue and subsequent histological control, could not prevail, in particular due to the considerable painfulness. Contrary thereto, the new composition can also be employed when the other therapeutic possibilities, i.e. radiotherapy and surgery, cannot be or can no longer be applied.

In actual fact, the composition leads by local application to an immediate intravital fixation of the tissue with which it comes into contact. The extent of its effect is strictly limited to the treatment spot. The immediate effect is displayed in a white-yellowish to grey coloration of the treated spot. The tissue devitalized in this way dries up and changes color to dark brown upon increasing mummification. The mummified scab detaches itself spontaneously after 2 to 5 weeks. The healing generally takes place without complications, especially without secondary infection, quickly and without leaving ugly scars or distortion of the surrounding tissue. The day after treatment, the patient can wash, bath or shower again. The composition is not resorbed and has no systemic effects. Sensitizing or allergic reactions have not been observed.

The said intravital fixation was examined on the composition of Example 7 by electron microscopy at the Laboratoire des Recherches sur les Tumeurs de la Peau humaine, Département de Dermatologie of the Fondation Adolphe de Rothschild, Paris; it could be shown thereby that it takes place very quickly and is of high quality. The structures of the Stratum corneum and the Stratum malpighii remain fully preserved, including such sensitive organella as the desmosoma and keratinosoma. These contain lytic enzymes which, in the case of a delayed fixation, would lead to their partial digestion.

It appears that the composition has a specific effect on hyperplastic, metaplastic and neoplastic tissues. A specific anticancerous effect of the composition or a special sensitivity of cancer cells to the composition could not be proven until now. The apparent specificity probably originates in a peculiarity of the tumor tissue which is actually looser and less dense and solid than normal, healthy tissue. The looser structure of tumor tissue can allow faster and easier penetration of the composition than the more solid cell assembly of healthy tissue; this tissue and in particular the subcutaneous collagen probably act as a barrier which prevents the composition spreading. This explains why the healthy cells of the surrounding area are not damaged or are only slightly damaged. The reparative ability of the surrounding, healthy cells does not only remain preserved but leads by phagocytosis and plasma cell reaction in connection with a proliferation of mesenchymal cells to fast regeneration and replacement of the tissue loss which occurred.

The metal ions apparently play an important role with regard to the penetration speed and the depth of penetration of the composition into the skin. By virtue of these factors or perhaps even directly, the metal ions presumably influence, at least partly, the reaction of the treated spot and that of the surrounding tissue and therewith also the mummification resp. healing speed.

The indications of the composition according to the invention are benign, premalignant and malignant lesions of the skin and mucous membranes, which are superficial or can be reached from outside, e.g.

basaloma, particularly in the case of reoccurrences near the scar after radiotherapy or surgery, near the eyes and on the nose or ears and in multiple occurrence;

other skin tumors, as long as they do not tend to form metastases in organs other than the skin;

benign cervix lesions, e.g. erosion of the portio;

epidermal nevi, fibroma of the skin and mucous membranes, senile keratoses, lentigo senilis, lentigo praemaligna;

seborrhoic warts (verruca senilis) and juvenile warts (verruca plana);

verruca vulgaris and condyloma acuminatum.

The following table lists the various types of tumors for which the composition is indicated, with the number treated in each diagnostic category documented in the noted references. The composition used was the one according to Example 6 or 13 (Solcogyn, reg. trade-name) in the gynaecological cases, according to Example 3 or 12 (Solcoderm, reg. trade-name) in all other cases.

TABLE 10

| Ref. | Verruca vulgaris | Verruca plana | Condyloma acuminatum | | Basaloma | | Keratosis | | Nevus | | Molluscum contagiosum |
| --- | --- | --- | --- | --- | --- | --- | --- | --- | --- | --- | --- |
| 1 | 6 | 1 | | 3 | | 29 | | 7 | | 6 | |
| 2 | 19 | | | 4 | | 26 | | 21 | | 41 | |
| 3 | | | | | (6) | 21 | | | | | |
| 4 | | | | | | 303 | | | | | |
| 5 | 24 | | (21) | 25 | (38) | 73 | | | | 4 | 1 |
| 6 | 1 | 1 | | | | 13 | | 5 | | 12 | |
| 7 | 8 | | | | | | | 12 | | 7 | |
| 8 | 2 | (5) 38 | (7) | 22 | (81) | 201 | (153) | 448 | (48) | 90 | |
| 9 | 1 | 6 | | 2 | | 4 | (17) | 20 | (8) | 15 | |
| 10 | 1 | 2 | | 1 | | 37 | | 27 | | | |
| 11 | 15 | | | | | | | | | 5 | 8 |
| 12 | | | | | | 9 | | 1 | | 10 | |
| 13 | | | | 35 | | | | | | | |

When ( ) appears, the number in the bracket is the number of patients, and the other is the number of lesions.

The reports and papers referred to in Table 10 as well as those mentioned hereinafter, which are numbered 1 to 16 and which all show the utility of the invention, are herewith incorporated by reference.

Double-blind clinical comparisons were designed with matched pairs of lesions in order to evaluate the therapeutic effects of various compositions according to or outside the invention.

In two small studies (14,15) involving 5 and 6 patients, respectively, 6.2 normal nitric acid and a same solution with added sodium nitrite were compared. The results are given in detail in the following table; they confirm the unexpected superiority of the new composition over nitric acid alone.

TABLE 11

| | No. superior/ total No. with nitrite | No. superior/ total No. without nitrite |
| --- | --- | --- |
| Less initial side effects | 10/11 | 0/11 |
| Better final mumification | 7/11 | 3/11 |
| Less final surrounding reaction | 7/11 | 1/11 |
| Better over-all rating | 6/11 | 2/11 |

Along the same lines as above more complex compositions, then, were compared with 6.2 normal nitric acid alone. The results of the over-all evaluation are summarized in the following table.

TABLE 12

| Composition | Number of Patients | Average Sore |
| --- | --- | --- |
| Nitric acid only (N) | 49 | 0.4 |
| Nitric + acetic acid (NA) | 20 | 1.0 |
| Nitric + oxalic acid (NO) | 20 | 1.5 |
| Nitric + oxalic + acetic acid (NOA) | 20 | 2.1 |
| Solcoderm (Example 3 or 12) | 33 | 2.6 |

The above data indicate that the preferred compositions, i.e. those in which an oxidizable organic acid generates nitric acid reduction products (NO, NOA and Solcoderm), are clearly better than plain nitric acid (N) or a composition comprising a non-oxidizable organic acid (NA). The results are statistically significant. For details of the comparison between nitric acid alone and Solcoderm (R) cf. M. Weiner et al. (16).

The advantages of the composition according to the invention and the method of intravital fixation based on its use can be summarized as follows:

1. The treatment is limited to pathologically altered parts of tissue which should be removed.
2. The loss of tissue resulting can be restricted to a minimum.
3. The scar remaining is mostly unobtrusive.
4. The surrounding tissue is not damaged.
5. The treatment is generally painless.
6. The treatment can be carried out ambulatory; the patient is subsequently not limited in his activities.
7. The treatment is of particular advantage, if multiple lesions are present, or if prior operations or radiotherapy exclude renewed surgery or radio-therapy.

In the following examples, when no other indication is given, the solution was stored at room temperature and in loosely closed bottles.

EXAMPLE 1

750 mg of sodium nitrite are placed in a measuring flask of 250 ml and 100 ml of water are poured in. The crystals dissolve; the temperature of the solution is 22.5° C. Then 128.5 ml of 65% nitric acid are added; the temperature rises to about 40° C. The solution turns pale yellow and produce nitrous gases. The solution is cooled in a water bath to about 25° C. and water is added up to 250 ml.

10 ml samples of the composition obtained were filled into 10 ml plastic bottles with screw-top, in order to determine their nitrate and nitrite contents at various time intervals. Some of the bottles were closed, the others were left open to stand at room temperature.

| Closed samples | | | |
| --- | --- | --- | --- |
| Age of composition | 70 mins. | 1 day | 7 days |
| Nitrate content | 502 | 499 | 458 mg/ml |
| Nitrite content | 1.03 | 1.26 | 0.59 |
| Open samples | | | |
| Age of composition | 165 mins. | 1 day | 7 days |
| Nitrate content | 518 | 485 | 493 mg/ml |
| Nitrite content | 1.10 | 0.25 | 0.003 |

EXAMPLE 2

0.077 g of copper(II)-nitrate-trihydrate, 8.64 g of cadmium nitrate tetrahydrate, 118.5 g of oxalic acid-dihydrate, 26.5 ml of 90% lactic acid, 0.85 ml of pyruvic acid, 80.1 ml of acetic acid and 500 ml of water of about 20° C. are mixed together. During stirring, the crystals gradually dissolve. After half an hour, 1014 ml of 65% nitric acid are added. The mixture warms to about 45° C. It is diluted with 200 ml of water and stirred for 18 hours; it gradually cools thereby to 22° C. Then it is diluted with water up to 2000 ml.

The analysis of the 5 month-old composition gave the following values:

| Specific weight | 1250 mg/ml |
|---|---|
| Acid equivalent | 9.15 mmol/ml |
| Dry weight[1] | 779 mg/ml |
| Content of $Cd^{2+}$ | 1.62 mg/ml |
| Content of $Cu^{2+}$ | 0.012 mg/ml |
| Oxalate content | 33 mg/ml |
| Lactate content | 6,8 mg/ml |
| Nitrate content | 464 mg/ml |
| Nitrate content | 0.15 mg/ml |
| Acetic acid content | 42 |

[1] always after neutralization and lyophilisation 6 months after production, the acid equivalent was 8.88 mmol/ml, the dry weight 755 mg/ml.

| 9 months after production: | nitrate content | 442 mg/ml |
|---|---|---|
| 10 months after production: | nitrite content | 0.015 mg/ml |
| 15 months after production: | nitrite content | 0.018 mg/ml |

EXAMPLE 3

0.086 g of copper(II)-nitrate-trihydrate, 113.5 g of oxalic acid-dihydrate, 41.1 ml of 90% lactic acid, 34.4 ml of acetic acid and 0.85 ml of pyruvic acid are dissolved in 600 ml of water of about 20° C. Within 10 minutes, 982 ml of 65% nitric acid are added. The mixture heats up to about 30° to 35° C. After 2 hours, it is diluted with water until its volume is 2000 ml.

The analysis results are from a 3½ month-old composition. The composition was analysed again 13 months after its production; in the meantime, it had turned green and gave off brown gases (NO₂) upon removal of the cap.

| Date of Production July 13, 1978 | | |
|---|---|---|
| Date of Analysis | 25.10.78 | 23.8.79 |
| Specific weight | 1246 | 1237 mg/ml |
| Acid equivalent | 8.66 | 10.06 mmol/ml |
| Dry weight | 738 | 840 mg/ml |
| $Cu^{2+}$-content | 0.015 | 0.014 mg/ml |
| Oxalate content | 34 | 46 mg/ml |
| Lactate content | 11 | <0.02 mg/ml |
| Nitrate content | 381 | 415 mg/ml |
| Nitrate content | 0.0013 | 4.15 mg/ml |
| Acetic acid content | 21 | 22 mg/ml |

EXAMPLE 4

124.4 g of oxalic acid-dihydrate, 27.9 ml of 90% lactic acid, 0.9 ml of pyruvic acid, 84.1 of acetic acid and about 500 ml of water at 20° C. are mixed together. While stirring continuously, 1065 ml of 65% nitric acid are added within 10 minutes. The temperature rises thereby to 30° C. The solution is colorless and clear; it is left to stand overnight at room temperature. Large crystals form. The mixture is heated to 25° C. and stirred; the crystals gradually dissolve. Then water is added up to a volume of 2000 ml. Small, colorless crystals are formed thereby. The mixture is left to stand for one week at room temperature. The supernatant (solution A, see below) is clear and colorless. In a measuring flask, 8.843 g of zinc nitrate hexahydrate are dissolved in water and the solution is diluted to 100 ml. 5 ml of this zinc nitrate solution are mixed with an amount of the above mentioned solution A until a volume of 100 ml is attained.

The analysis of the composition immediately after its production gave the following values:

| Specific weight | 1255 mg/ml |
|---|---|
| Acid equivalent | 9.13 mmol/ml |
| Dry weight | 800 mg/ml |
| Content of $Zn^{2+}$ | 1.00 mg/ml |
| Oxalate content | 34 mg/ml |
| Lactate content | 12 mg/ml |
| Nitrate content | 483 mg/ml |
| Nitrite content | 0.0009 mg/ml |
| Acetic acid content | 26 mg/ml |

6 months after production, the nitrite content was only about 0.0001 mg/ml. In order to bring the composition to the minimum nitrite content of 0.01 mg/ml, 10 mg of sodium nitrite were dissolved in the final solution, nitrous gas developed immediately, the solution remained colorless. A sample of the solution was taken, immediately diluted with water and analysed half an hour later. The nitrite content, calculated on the undiluted solution, was 0.019 mg/ml (i.e. 30%, calculated on the added sodium nitrite).

EXAMPLE 5

300 ml of water at 20° C. are added to a mixture of 4.812 g of silver nitrate, 59.867 g of oxalic acid-dihydrate, 40 ml of glacial acetic acid and 13.23 ml of 90% lactic acid. The crystals dissolve partly. Within 5 minutes, 507 ml of 65% nitric acid are added dropwise under continuous sitrring. The temperature rises thereby to 31° C. 15 minutes after adding the nitric acid, all the crystals have dissolved; the solution is clear and colorless. It is diluted with water until its volume is 1000 ml and then left to stand at room temperature. During the course of the next 3 days, large colorless crystals form which are removed by filtering off. The analysis of the composition immediately after its preparation (on Jan. 26, 1979) gave the following values:

| Specific weight | 1255 mg/ml |
|---|---|
| Acid equivalent | 8.31 mmol/ml |
| Dry weight | 707 mg/ml |
| Content of $Ag^+$ | 3.17 mg/ml |
| Oxalate content | 34 mg/ml |
| Lactate content | 12 mg/ml |
| Nitrate content | 420 mg/ml |
| Nitrite content | 0.0037 mg/ml |
| Acetic acid content | 32 mg/ml |

During the course of 6 months, a minimal green coloring can be seen; 217 days after preparation, a renewed analysis showed a nitrite content of 1.32 mg/ml.

EXAMPLE 6

285.2 g of L-tartaric acid and 8.330 g of zinc nitrate-hexahydrate are placed in a 2000 ml measuring flask and about 600 ml of water is poured in. A part of the crystals dissolves. Then, within 15 minutes, 1013.2 ml of 65% nitric acid are added; by cooling in a water bath, one ensures that the temperature of the flask's contents does not exceed 25° C. Finally, it is filled up with water up to 2000 ml. With the help of a magnetic stirrer, the solution is stirred until all the crystals have dissolved; the solution is clear and colorless. In the course of a year, stored in the closed measuring flask, the solution turns green and produces brown gases (NO₂) when the cap is removed. Furthermore, small, colorless crystals gradually separate off.

| Date of Production May 22, 1978 | | | |
|---|---|---|---|
| Date of Analysis | 31.5.78 | 20.6.78 | 16.8.79 |
| Specific weight | 1296 | — | 1238 mg/ml |
| Acid equivalent | 9.47 | 9.42 | 7.79 mmol/ml |
| Dry weight | 884 | 844 | 667 mg/ml |
| $Zn^{2+}$-content | 1.07 | — | 0.83 mg/ml |
| Oxalate content | — | 0 | 39 mg/ml |
| Nitrate content | 530 | 523 | 369 mg/ml |
| Nitrite content | — | — | 4.45 mg/ml |

EXAMPLE 7

1.5 g of metallic cadmium and 22.5 g of metallic copper are dissolved in 1000 ml of 65% nitric acid. While stirring strongly and cooling slightly with the help of a water bath of about 20° C., 230 g of 80% lactic acid are added dropwise within 30 minutes. Subsequently, 50 ml of 40% ethanol are added dropwise within 20 minutes. During the addition of the ethanol, the temperature of the reaction mixture rises to 35° to 40° C. Shortly after adding the ethanol, a pale blue precipitate forms. 3 hours after adding the ethanol, 1 g of oxalic acid-dihydrate are added, 10 minutes later 1 g of maleic acid and a further 10 minutes later 15 ml of pyruvic acid. The water bath is now adjusted to 35° to 40° C. As soon as the reaction mixture has reached this temperature, 20 ml of acetic acid are added dropwise within 10 minutes. The mixture is stirred continuously for a week at 35° to 40° C.; then it is stored at room temperature. It should only be lightly closed as it is still forming bubbles. By occasionally shaking the liquid, the bubbles can escape more easily and the maturation process is furthered. The maturation process is finished when the liquid has become clear and colorless and no further bubbles are formed. The supernatant is then decanted from the precipitate; only the supernatant is used as a medicine.

EXAMPLE 8

While stirring, 137 ml of water, 171 g of copper(II)-nitrate-trihydrate and 8.23 g of cadmium nitrate-tetrahydrate are added to 1798 ml of 65% nitric acid. The salts dissolve; immediately after this, 338 ml of 90% lactic acid are added dropwise within 30 minutes. Within the next 30 minutes, a mixture of 47 ml of absolute ethanol and 56 ml of water is added dropwise. 15 minutes after adding the last of the ethanol, a formation of gas begins and the solution heats up. As soon as it has reached a temperature of 40° C., it is cooled from the outside with cold water and ice; the temperature gradually falls to about 30° C. 3 hours after adding the last of the ethanol, 2 g of oxalic acid-dihydrate, 2 g of maleic acid and 30 ml of pyruvic acid are added within 10 minutes, and, after a break of 10 minutes, also 40 ml of glacial acetic acid. The temperature is kept at about 30° C. The mixture is stirred for another 24 hours. Subsequently, it is left to stand at room temperature and then further processed according to Example 7.

EXAMPLE 9

40.9 g of 90% lactic acid, 5 ml of absolute ethanol, 3 ml of pyruvic acid, 0.2 g of oxalic acid-dihydrate, 0.2 g of maleic acid, 4 ml of glacial acetic acid, 0.823 g of cadmium nitrate-tetrahydrate and 17.11 g of copper(II)-nitrate-trihydrate are added to 18.7 ml of water. The mixture is stirred and heated to 50° C. Under these conditions, the crystals dissolve to a large extent. Within an hour, 180 ml of 65% nitric acid are added dropwise. A clear, dark blue solution ensues. It is cooled to 20° C. and left to stand for 3 days. During this time, no reaction is observed. On the fourth day after beginning production, the solution is heated to 50° C. It begins to foam and forms nitrous gases. The temperature rises within 10 minutes to 78° C. and a light blue, fine-grained precipitate is formed. The mixture is cooled to 50° C. with cold water, kept at this temperature for a further 8 hours while being stirred and is finally left to stand at room temperature and further processed according to Example 7.

EXAMPLE 10

20.5 g of 90% lactic acid, 2.5 ml of absolute ethanol, 1.5 ml of pyruvic acid and 0.1 g of maleic acid are mixed together. Within 30 minutes, 90 ml of 65% nitric acid are added dropwise at 20° C. The solution remains clear and colorless. Then 0.1 g of oxalic acid-dihydrate, 2.0 ml of glacial acetic acid, 0.412 g of cadmium nitrate-tetrahydrate, 8.55 g of copper(II)-nitrate-trihydrate and 9.4 ml of water are added. A deep blue solution is formed. It is stirred for an hour at 55° C. without showing any reaction. Subsequently, the solution is left to stand for 16 hours at room temperature. During the subsequent heating to 50° C., nitrous gases start to form and a fine-grain, light blue precipitate starts to separate. The mixture is stirred for 4 hours at 55° C. and is then left to stand at room temperature and further processed according to Example 7.

| | Analysis Results | | | |
|---|---|---|---|---|
| | Example | | | |
| | 7 | 8 | 9 | 10 |
| Age of composition | 385 days | 195 days | 24 days | 20 days |
| Specific weight | 1236 | 1244 | 1268 | 1270 mg/ml |
| Acid equivalent | 838 | 8.64 | 9.21 | 9.46 mmol/ml |
| Dry weight | 778 | 740 | 797 | 826 mg/ml |
| Content of $Cd^{2+}$ | 1.52 | 1.50 | 2.15 | 1.51 mg/ml |
| Content of $Cu^{2+}$ | 0.013 | 0.011 | 0.055 | 0.014 mg/ml |
| Oxalate Content | 40 | 39 | 35 | 33 mg/ml |
| Lactate Content | 4.7 | 14 | 20 | 37 mg/ml |
| Nitrate Content | 381 | 349 | 428 | 460 mg/ml |
| Nitrite Content | 0.099 | 0.10 | 0.28 | 0.68 mg/ml |
| Acetic acid content | 38 | 41 | 32 | 28 |

EXAMPLE 11

A composition prepared as in Example 7 according to the oxidative method shows the following contents after 1-year's standing with a loose seal:

| Specific weight | 1246 mg/ml |
|---|---|
| Acid equivalent | 8.62 mmol/ml |
| Dry weight | 787 mg/ml |
| Content of $Cu^{2+}$ | 0.011 mg/ml |
| Content of $Cd^{2+}$ | 1.50 mg/ml |
| Oxalate content | 42 mg/ml |
| Lactate content | 12 mg/ml |
| Nitrate content | 394 mg/ml |
| Nitrite content | 0.179 mg/ml |
| Acetic acid content | 44 |

About 15 months after its production, a sample of this composition was filled into a plastic, screw-top bottle and was left to stand at room temperature with hermetic seal (screw-top tightly closed). After 3 weeks, the contents of the bottle had turned green and produced considerable gas bubbles upon removing the cap; the bubbles contained NO₂ (brown, smell). By squeezing, shaking and blowing into the plastic bottle, a large part of the gas dissolved in the liquid could be expelled. If the cap was screwed on again and the bottle shaken, the inner-pressure increased and, upon removal of the cap, the solution foamed, releasing NO₂. The nitrite determination of the sample in the bottle now showed, even after repeated shaking and blowing the gas out, a nitrite content of 25.93 mg/ml, while the main portion of the composition kept under loose seal had a nitrite content of 0.089 mg/ml. Both the contents of the bottle and the main portion of the composition were subjected to a second nitrite analysis after a small sample of the two liquids had stood for 24 hours in an open container. After this, the contents of the bottle had a nitrite value of 0.015 mg/ml, the main portion still 0.001 mg/ml.

The change which the contents of the bottle underwent while standing under hermetic seal is due to the fact that the hermetic seal prevents the slowly-forming gases from escaping and leads to a pressure increase within the container which apparently accelerates the oxidative decomposition of the oxidizable substances, until a balance is achieved.

Corresponding changes, accompanied by the discoloration to blue/green and the formation of nitrous gases, are also observed with compositions prepared by mixing. This was observed, among others, on the compositions of examples 3 and 6 and substantiated by analytical findings. Both compositions were originally colorless and did not develop any gas bubbles during the first months after their production. The composition of example 3 had a lactate content of 11 mg/ml and a nitrite content of 0.0013 mg/ml three and a half months after its production. About 8 months after its production, the green color was observed for the first time. 10 months after the first analysis, the composition—now distinctly green in color—was again analyzed. This time it had 4.15 mg/ml of nitrite; lactate could no longer be found at all, contrary to the first analysis. Significant, if less extreme, differences were also observed in the acid equivalent (increase), dry weight (increase) and oxalate content (increase), while a slight increase of the nitrate content was not considered a significant change.

The composition of example 6, produced from tartaric acid, zinc nitrate and nitric acid was also colorless originally and showed no tendency to develop gas bubbles. The analysis which took place a month after its production gave the same values as that carried out 10 days after production; no oxalic acid was found upon analysis after one month. Five months after production, a somewhat lower acid equivalent was found; at that time, there was no distinct coloration to be seen. 15 months after preparation, the composition was distinctly green. It now contained 39 mg/ml of oxalate and 4.45 mg/ml of nitrite. Significant changes were further shown by the acid equivalent (decrease), the dry weight (decrease) and the nitrate content (decrease).

The changes described, recognizable from the discoloration to green and the release of nitrous gases, do not occur equally quickly. The change in the composition in the plastic bottle, for instance, (example 7) took place within a few weeks and lead to a nitrite content which must have been considerably higher than 25.93 mg/ml before opening the bottle which had a very high inner pressure. However, in both of the other compositions (examples 3 and 6) the coloration could not be recognized until after several months. The differences, also the varyingly high nitrite contents of the colored solutions, are apparently due to the fact that the one composition only had a very small amount of air space inside the hermetically sealed container, while the other two compositions had relatively large volumes of gas available. Furthermore, the speed of the change appears to depend upon the tightness of the seal. For instance, with the composition according to example 2, no coloring to green and no gas-formation was observed, although it was stored in the same sort of container as the compositions of examples 3 and 6; it is to be supposed that the glass plug over the composition of example 2 did not seal hermetically.

Finally, it is also to be noted that the oxalate content of all compositions lies at about 40 mg/ml. Even the composition of example 6 which was originally oxalate-free shows an oxalate content of this order, which presumably corresponds to the content of the saturated solution.

The nitrile content of a sample does not only depend upon the seal of the container and so upon the speed of the formation of the nitrous gases, but also from the speed of escape. This is clearly shown if the compositions of examples 3, 6 and 7 (bottles) are compared with that of example 1. In the former case, the liquids which were rich in nitrite were left to stand overnight in a flat dish; the gases could escape from the liquid without obstruction, could fill the desiccator and gradually leave it through its opening. However with example 1, only the cap of a bottle was left unscrewed; it was less easy here for the gas molecules to leave the liquid. These differences are shown clearly from the nitrite contents found after 24 hours. In the case of the three liquids which had stood in flat dishes, it had fallen to around a thousand of its original level (from 4.15 to 0.005; from 4.45 to 0.004; from 25.93 to 0.015), while it only sank to a quarter in example 1 (in the bottle) and needed a week to sink further.

EXAMPLE 12

114.61 g of oxalic acid, dihydrate, and 600–800 ml of water are put in a 2 liter volumetric flask, warmed up to 50°–60° C. and gently shaken until the crystals have dissolved. Then the solution is cooled to about 40° C. 76 ml of glacial acetic acid, 908 ml of concentrated nitric acid (containing 14.4 mol/l HNO₃) and 91.3 mg of cupric nitrate, trihydrate, are added. The crystals easily dissolve when the mixture is shaken. After cooling down to 20° C., 9.18 ml of 90 percent lactic acid are added. The solution is then diluted with water to a final volume of 2000 ml.

EXAMPLE 13

114.61 g of oxalic acid, dihydrate, and 600–800 ml of water are put in a 2 liter volumetric flask, warmed up to 50°–60° C. and gently shaken until the crystals have dissolved. Then the solution is cooled to about 40° C. 41 ml of glacial acetic acid, 830 ml of concentrated nitric acid (containing 14.4 mol/l HNO₃) and 11.83 g zinc nitrate, hexahydrate, are added. The mixture is shaken until the crystals have dissolved. The solution is then cooled down to 20° C. and diluted with water to a final volume of 2000 ml.

We claim:

1. A method for the local treatment of human skin disease selected from the group consisting of verruca vulgaris, verruca plana, condyloma acominatum, keratosis, nevus molluscum contagiosum and of basaloma which comprises applying to said human skin an effective amount of an aqueous solution comprising
(1) nitric acid in a concentration and amount which give the solution a pH value of below 1 and an acid equivalent of from about 6 to 10 millimole/ml, and
(2) nitrous acid, in an amount corresponding to about 0.01 to 5 mg of nitrite per ml and which, when stored at room or lower than room temperature, proves stable as regards the respective range of concentration of components 1 and 2.

* * * * *